United States Patent [19]

Bosma et al.

[11] Patent Number: 5,760,859
[45] Date of Patent: Jun. 2, 1998

[54] RETARDATION LAYER HAVING A DISPERSION ADAPTED TO THE ACTIVE LIQUID-CRYSTALLINE CELL

[75] Inventors: Martin Bosma; Jan-Willem Venema; Stephen James Picken, all of Arnhem; Gustaaf Ronald Möhlmann, Dieren, all of Netherlands

[73] Assignee: Akzo Nobel NV, Arnhem, Netherlands

[21] Appl. No.: 619,613

[22] PCT Filed: Sep. 29, 1994

[86] PCT No.: PCT/EP94/03246

§ 371 Date: May 17, 1996

§ 102(e) Date: May 17, 1996

[87] PCT Pub. No.: WO95/09379

PCT Pub. Date: Apr. 6, 1995

[30] Foreign Application Priority Data

| Sep. 29, 1993 | [EP] | European Pat. Off. | 93202788 |
| Jul. 26, 1994 | [NL] | Netherlands | 9401217 |
| Aug. 19, 1994 | [NL] | Netherlands | 9401342 |

[51] Int. Cl.⁶ .................. G02F 1/1335; G02F 1/1347
[52] U.S. Cl. .................. 349/75; 349/76; 349/117; 349/183; 428/1
[58] Field of Search .................. 349/117, 75, 182, 349/183, 187, 76; 428/1; 252/299.01; 359/494, 500

[56] References Cited

U.S. PATENT DOCUMENTS

| 4,954,288 | 9/1990 | East | 349/197 |
| 5,142,393 | 8/1992 | Okumura et al. | 349/119 |
| 5,308,535 | 5/1994 | Scheuble et al. | 252/299.01 |
| 5,380,459 | 1/1995 | Kanemoto et al. | 349/76 |
| 5,519,523 | 5/1996 | Madokoro et al. | 349/181 |
| 5,576,077 | 11/1996 | Bosma et al. | 349/96 |

FOREIGN PATENT DOCUMENTS

| 0 380 338 | 8/1990 | European Pat. Off. | G02F 1/1335 |
| 0 382 460 | 8/1990 | European Pat. Off. | G02F 1/1335 |
| 0 524 028 | 1/1993 | European Pat. Off. | G02F 1/1335 |
| 0 550 105 | 7/1993 | European Pat. Off. | C09K 19/38 |
| 39 25 382 | 1/1991 | Germany | C09K 19/52 |
| 1-206318 | 8/1989 | Japan | 349/117 |

OTHER PUBLICATIONS

International Search Report in PCT/EP94/03246 dated Jan. 31, 1995.
W.H. deJeu, *Physical Properties of Liquid Crystals*, p. 23 (1st ed. 1980).
Jun-ichi Hirakata, et al., "A Monochromatic Black and White Supertwisted Nematic Liquid Crystal Display with a Single Cell and a Birefringent Film" 30 *Japanese J. of Applied Physics*, pp. 682–686 (Apr. 1991).
Kirk–Othmer, *Encyclopedia of Chemical Technology*, vol. 7, pp. 728–730 (3rd ed. 1979).
E.P. Raynes, "The Optical Properties of Supertwisted Liquid Crystal Layers" 4 *Molecular Crystals & Liquid Crystals Letters*, pp. 69–75 (Feb. 1987).

Primary Examiner—William L. Sikes
Assistant Examiner—Tai V. Duong
Attorney, Agent, or Firm—Loretta A. Miraglia; Louis A. Morris

[57] ABSTRACT

The invention is in the field of retardation layers comprising high-molecular weight liquid-crystalline material for liquid-crystalline displays. The invention is directed to a retardation layer for a liquid-crystalline display comprising high-molecular weight liquid-crystalline material, wherein the dispersion has been adapted to that of the active liquid-crystalline cell by varying the mesogenic groups of the high-molecular weight liquid-crystalline material, so that the difference in dispersion between the active cell and the retardation layer in the wavelength area of 400–800 nm is not more than 0.1.

8 Claims, 3 Drawing Sheets

RETARDATION LAYER HAVING A DISPERSION ADAPTED TO THE ACTIVE LIQUID-CRYSTALLINE CELL

The invention is in the field of retardation layers comprising high-molecular weight liquid-crystalline material. Such retardation layers are used in displays. FIG. 1 is a schematic depiction of the construction of a display.

FIG. 1 shows a cross-section of a display comprising an active twisted layer (4), the active cell, which can be switched on and off by means of transparent electrodes (6), and a retardation layer (3), with substrates (2) disposed on either side of the two layers (3) and (4). At the outer sides of the two outermost substrates there are polarisers (1), and underneath the polariser situated under the active twisted layer is positioned a mirror (5).

DESCRIPTION OF THE RELATED ART

In practice, the mirror can be omitted in some displays. The invention is directed in particular to the retardation layer (3) of a display. Retardation layers serve to compensate for the undesirable birefringence effect that occurs in the active cell in the display. For the retardation layer use may be made of a twisted nematic layer composed of low-molecular weight liquid-crystalline material such as is described in, e.g., Kirk Othmer's *Encyclopedia of Technology*, 3rd ed. (New York: Wiley & Sons) Vol. 7, p. 728. Although low-molecular weight liquid-crystalline material gives good compensation when used, it is attended with the drawback of being low-viscous. For that reason, the low-molecular weight material is sealed between inflexible substrates by means of spacers in order to attain a twisted, form-retaining structure. In other words, a closed, rigid cell has to be made.

Alternatively, use may be made of birefringent films, e.g., a film of drawn polymer such as a birefringent polycarbonate film. Such a birefringent polycarbonate film is described in *Jap. J. Appl. Physics*, Vol. 30, No. 4 (April 1991), 682–686. By using birefringent polycarbonate films a liquid-crystalline display of reduced thickness and weight may be obtained. However, said birefringent polycarbonate films fail to provide optimum contrast.

The reason for this poor contrast is as follows:

As stated above, retardation layers serve to compensate for the undesirable birefringence effect that occurs in the active cell of a display. This birefringence effect depends on the retardation value, the angle of twist, and the direction of twist of the layer of liquid-crystalline molecules in the active cell of the display. The retardation of a birefringent layer is defined as the product of the birefringence value ($\Delta n$) and the layer thickness. At a given wavelength, the birefringence effect of the active cell of the display can be completely compensated for by using a retardation layer that has equal retardation, and an equal as well as an opposite angle of rotation compared with the active cell. For full compensation these conditions should apply for the entire visible part of the wavelength spectrum. This requirement can only be realised if the dependence of the birefringence on the wavelength, also known as the dispersion, of the material of the retardation layer is equal to that of the LC material used in the active cell of the display. This is not the case for birefringent polycarbonate films. The dispersion of birefringent polycarbonate films is lower than liquid crystalline active cells which are commercially used. Therefore, their retardation can only be set (by setting the layer thickness) to match the retardation of the active cell at 550 nm. As a consequence, over the rest of the visible wavelength area the retardation fails to match that of the active cell of the display, especially in the wavelength area of 400–550 nm the dispersion appears to be too low. This results in a less than optimal contrast.

In DE 39 25 382 A1 it is acknowledged that the optical properties of the compensating film (i.e., the retardation layer) should have a wavelength dependency which is substantially identical to that of the liquid-crystalline layer used for displaying information ( i.e. the active liquid-crystalline cell). Further, DE 39 25 382 teaches that a retardation layer containing a liquid-crystalline polymer is more suitable than a layer consisting of stretched polycarbonate when is comes to the desired compensation.

However, DE 39 25 382 A1 does not teach how the dispersion of the retardation layer can be matched very precisely with the dispersion of a specific active liquid-crystalline cell.

DESCRIPTION OF THE INVENTION

In the present invention a retardation layer of high-molecular material is provided which has a retardation virtually matching that of the active cell over the whole visible wavelength area. Accordingly, the invention is directed to a method for preparing a liquid-crystalline display, which display comprises an active liquid-crystalline cell and a retardation layer containing a high-molecular weight liquid-crystalline material, wherein the dispersion of the retardation layer is adapted to that of the active liquid-crystalline cell by varying the mesogenic groups of the high-molecular weight liquid-crystalline material, so that the difference in dispersion between the active cell and the retardation layer in the wavelength area of 400–800 nm is not more than 0.1, preferably not more than 0.03.

DETAILED DESCRIPTION OF THE INVENTION

Figure 1:
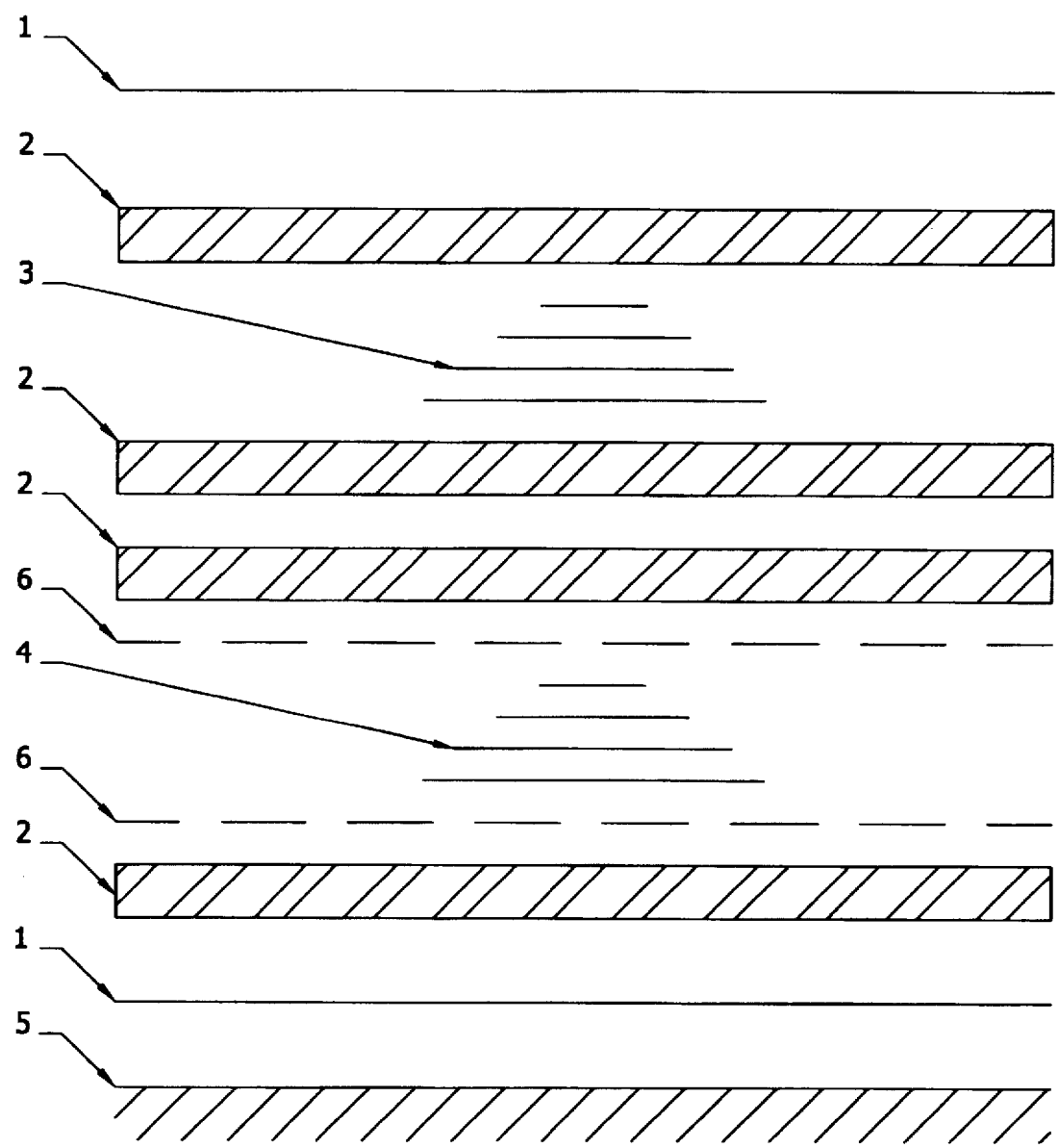
FIG. 1 is a schematic depiction of the construction of a display.

By high-molecular weight liquid-crystalline material are meant: relatively low-molecular weight liquid-crystalline polymers, oligomers, and liquid-crystalline glasses. The molecular weight for liquid-crystalline glasses and oligomers varies from 1000 to 4000, for liquid-crystalline polymers it varies 1000 to 20 000. High-molecular weight liquid-crystalline material has a higher mechanical strength than low-molecular weight liquid-crystalline material. Therefore, it is not necessary to seal the liquid-crystalline material in a rigid cell. Because liquid-crystalline material is used, and the mesogenic groups of liquid-crystalline material can easily be varied, it is possible to obtain a retardation layer which has approximately the same dispersion as that of the active cell.

The dispersion is defined here as the retardation (or the birefringence) at a certain wavelength divided by the retardation (or the birefringence) at 550 nm.

It appears that the dispersion of a liquid-crystalline material can be varied by the following measures:

By using mesogenic groups with large conjugated systems the dispersion of liquid-crystalline material is increased, whereas smaller conjugated systems lower the dispersity, especially in the wavelength area of 400–550 nm. Usually, mesogenic groups have the following general formula:

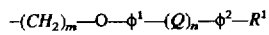

wherein:

m stands for an integer from 0–6,

Q stands for —C(O)—O—, —C=C—, —C=N—, —N=C—, —O—C(O)—, —C≡C— or —N=N—,

R¹ stands for —O—R², —NO₂ —CN, —HC=C(CN)₂, —C(CN)=C(CN)₂ or —R²,

φ¹ stands for a substituted or unsubstituted cyclic, aromatic or heterocyclic compound having 4–10 carbon atoms, φ² (stands for a cyclic, aromatic or heterocyclic compound having 4–10 carbon atoms, n stands for 0 or 1.

If for Q groups such as —C=C—, —C=N—, —N=C—or —C≡C—are used, or if n is O, the mesogenic group has a large conjugated system. By using —C(O)—O—or —O—C(O)—the conjugation is decreased. The conjugation can be further decreased by using —O—R² or R² for the R¹ end group of the mesogenic group. If for φ¹ or φ² a non-aromatic cyclic compound is used, the dispersity will be lower than when aromatic compounds are used.

By using mesogenic groups with polar moieties the dispersion of the liquid-crystalline material is increased. For instance, if mesogenic groups according to formula 1 are used with —NO₂ as R¹ instead of O—R² or R², the dispersion is increased. Halogenation of the mesogenic group also gives an increase of dispersion.

When the dispersion of a commercially available active cell is known, the artisan can easily adjust the dispersion of the retardation layer via the measures described above. The birefringence at a certain wavelength can easily be measured with a refractometer, and from birefringences at various wavelengths the dispersion can be calculated. The retardation of a commercially available cell can be measured with various optical techniques known to the artisan. From the retardation at a certain wavelength and the retardation at 550 nm the dispersion at a certain wavelength can be calculated.

For accurate matching of the dispersion of an active cell, liquid-crystalline material may be used wherein both mesogenic groups having a large conjugated system and mesogenic groups having a smaller conjugated system are present. By varying the ratio of the two kinds of mesogenic groups the dispersion can be accurately matched with the active cell.

Examples of the cyclic or aromatic compounds φ¹ and φ² include:

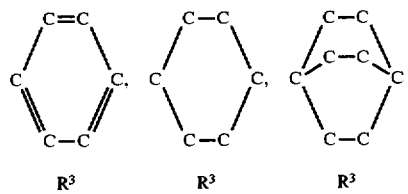

wherein R³ stands for an alkyl group having 1–5 carbon atoms.

Examples of R² groups include:

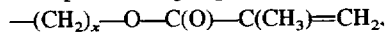
—(CH₂)ₓ—O—C(O)—CH=CH₂,
—(CH₂)ₓ—CH₃,
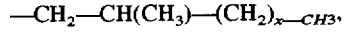
—CH(CH₃)—(CH₂)ₓ—CH₃, wherein x=1–14.

Some of these R² groups contain an asymmetrical carbon atom. The use of chiral (exc[us]ively laevorotatory or dextrorotatory) R² groups may be advantageous in LCD retardation layers, as will be explained below.

It was found that the dispersion of high-molecular weight liquid-crystalline material is mainly dependent on the mesogenic group. A specific mesogenic group gives the virtually same dispersion irrespective of the liquid-crystalline polymer, oligomer or glass into which it is incorporated.

As mentioned above, high-molecular weight material has a higher mechanical strength than low-molecular weight material. This makes it possible to place the liquid-crystalline material between glass substrates having a thickness of 20–500 micrometers instead of thick glass substrates. The liquid-crystalline material may even be placed between or coated on flexible plastic substrates such as PET and polycarbonate.

To obtain full compensation for the birefringence effect of the active cell, it is also necessary for the retardation layer to have an equal as well as an opposite angle of rotation compared with the active cell. A twisted structure is obtained by placing the liquid-crystalline material between two orienting substrates, giving one of the substrates a different orientation direction from that of the other substrate.

Various techniques are known for making an orienting substrate. For instance, the substrate itself may be rubbed in a single direction. The substrate in that case may be made of, e.g., polyimide, polyvinyl alcohol, glass, etc. Alternatively, the substrate may be provided with a thin orienting layer. This may be a thin polymer layer which can be rubbed, e.g., polyimide, polyvinyl alcohol, etc. Alternatively, this thin orienting layer may be a SiOₓ layer evaporated at an angle of less than 90°, usually of 60° or 86°. Generally, a substrate of poor flexibility, such as glass or quartz, is used for SiOₓ evaporation. These orienting techniques are known to the skilled person and require no further elucidation here. Of course, it is also possible to employ other orienting techniques.

To control the direction of rotation of the director (to the left or to the right) and/or to obtain an angle of rotation greater than 90°, the liquid-crystalline material is frequently mixed with a chiral material: the so-called chiral dopant. In principle, any optically active compound may be used to this end. As examples may be mentioned cholesterol derivatives and 4-(4-hexyloxy-benzoyloxy) benzene acid 2-octyl-ester. Ordinarily speaking, up to 5 wt. % of chiral dopant is employed in relation to the total amount of liquid-crystalline material. Alternatively, the liquid crystalline material itself may be provided with chiral centres. Preferably, this is done by providing the mesogenic group with a chiral chain (group $R_2$) or spacer, since in this way the transition temperatures will hardly if at all be adversely affected. Examples of mesogenic groups with chiral chains have been described above.

The angle of rotation of an STN display cell typically is 240° but may be any other appropriate value. In the case of an angle of rotation of 90° (or −90°), the film is generally called "twisted nematic." For a TFT-TN compensation layer an angle of rotation of 90° (or −90°) is required. If the angle of rotation is greater, the film is called "supertwisted nematic." In addition, this invention also concerns retardation layers with a smaller angle of rotation, from 0° (no twist) to 90° (or −90°). For convenience these layers are also called "twisted nematic" here. In the case of an angle of rotation of 0°, the arrangement of the liquid-crystalline layer will be uniform planar. At angles of rotation exceeding 360° the structure goes through more than one full rotation within a single layer. The length covered by the structure in a full rotation is called the pitch. The invention is also directed to retardation layers having more than one pitch (even more than 5 pitches).

The value of optical retardation ($=\Delta n$ (birefringence) X d (thickness of the (S)TN layer) may be adjusted by choosing an appropriate value for the thickness of the layer. This can be done by using spacers of appropriate size. In general, glass spheres, polymer spheres or silica spheres are used as spacers.

Alternatively, the high molecular-weight liquid-crystalline film can be placed between the substrate of the display cell and another substrate. In a further embodiment of the invention the LC polymer film is placed between the polariser and a substrate. In these embodiments of the invention a second substrate is not necessary and the thickness and weight of the retardation layer are reduced further.

The invention is further directed to a liquid crystalline display obtainable by the methods described hereinbefore. Further, the invention is directed to said liquid-crystalline display wherein both mesogenic groups having a large conjugated system and mesogenic groups having a smaller conjugated system are present.

The invention will be further illustrated with reference to the following unlimitative Examples.

EXAMPLES

Example 1

Liquid-crystalline glasses were prepared from mesogenic group-containing epoxides and diamines.
Synthesis of LC glasses (general method):

A mixture of 1 eq. of diamine and 4 eq. of epoxy was heated for 5 hours under a nitrogen atmosphere at a temperature of 130° C. The melt was cooled down and dissolved in THF, and the solution of approximately 20% (m/M) was precipitated in a 10-fold excess of ethanol. The yields were in the range of 75 to 90%.
epoxide of cyanobiphenyl A mixture of 39.0 g (0.20 mole) of hydroxycyanobiphenyl, 100 ml (1.25 moles) of epichliorohydrin, and 0.44 g (2.4 mmoles) of benzyl trimethyl ammonium chloride was heated to 70° C. Next, a solution of 17 g (0.42 mole) of sodium hydroxide in 100 ml water was dispensed in 3 hours. Following this addition there was one extra hour of stirring at 70° C. The reaction mixture was cooled to 20° C., and 200 ml of dichloromethane were added. The organic layer was separated from the aqueous one and washed with, successively, NaCl solution (twice) and water (twice). After drying on magnesium sulphate and concentration by evaporation the crude product was converted to the crystallised form from 450 ml of methanol. The yield was 38.30 g (76%).

The epoxide of cyanobiphenyl was used to prepare an LC glass (LC 1) by the general method for the synthesis of LC glasses specified above, using m-xylylene diamine (m-XDA), ex "FLUKA®" (Fluka Chemie AG, St. Gallen, Switzerland. The molecualar weight was found to be 1140, Tg: 64°/70° C., Tc: 127° C.
epoxide of methoxyphenyl benzoate
Preparation of 4-methoxyphenol-4'oxybenzoate 74.5 g (0.6 mole) of 4-methoxyphenol, 55.3 (0.40 mole) of hydroxybenzoic acid, and 1.24 g (20 mmoles) of boric acid were dissolved in 750 ml of toluene. Next, 2.0 g (20.4 mmoles) of $H_2SO_4$ were added dropwise, and the mixture was refluxed the formed water being distilled off azeotropically. The toluene was evaporated, and the reaction product was washed twice in 200 ml of diethyl ether/petroleum ether (1:1 (V:V)). The product was twice converted to the crystallised form from 400 ml of acetonitrile and then dried. The yield was 56.1 g (49%).

A mixture of 42.0 g (0.17 mole) of 4-methoxyphenol-4'oxybenzoate, 100 ml (1.25 moles) of epichlorohydrin, and 0.35 g of benzyl trimethyl ammonium chloride was heated to 70° C. Next, a solution of 6.4 g (0.16 mole) of sodium hydroxide in 32 ml of water was dispensed in 2 hours. Following this addition stirring continued for 2 more hours at 70° C. The reaction mixture was cooled to 20° C., and the organic layer was separated from the aqueous one and washed with 50 ml of water. The excess epichlorohydrin was removed by means of vacuum evaporation at a temperature below 50° C. The residue was dissolved in 250 ml of butanol/toluene (1:2 (V:V)) and stirred for 1 hour at 30° C. in the presence of a 20%-solution of NaOH (1.49 g). The organic layer was washed with water several times. After vacuum evaporation the crude product was twice converted to the crystallised form from methanol. The yield was 28.5 g (55%).

A liquid-crystalline glass (LC 2) was prepared by the general method for the synthesis of LC glasses specified above using methylene diamine, ex "FLUKA®" (Fluka Chemie AG, St. Gallen, Switzerland). The molecular weight turned out to be 1398, Tg: 66°/72° C., Tc: 127° C.

Example 2

Liquid-crystalline polyethers were prepared from mesogenic groupcontaining epoxides and mesogenic group-containing diols.
Synthesis of LC polyethers (general method):

To a mixture of OH-containing compound and 5% of $BF_3Et_2O$ in dichloromethane there was slowly added dropwise, at room temperature, epoxide dissolved in dichloromethane. In the case of acrylate alcohols being used, a pinch of "IONOL®" (Shell Chemical Corp., New York, N.Y.) was added. The polymerisation mixture was stirred overnight and then neutralised with solid CaO. After one hour the CaO was filtered off. The polyether was precipitated in ether, washed with ether, and dried under vacuum. The yield was 75–90%.

The epoxide of methoxyphenyl benzoate was used to prepare a liquid-crystalline polyether (LC 3) by the general method for the synthesis of LC polyethers specified above, using methoxyphenyl-(2,3 dihydroxypropyloxy)benzoate with an epoxy/OH ratio of 5:1. The diol was prepared in the same manner as the hexyloxy analogon in EP-A2-0 550 105. The molecular weight turned out to be 2984, Tg: 46°/52° C., Tc: 146° C.

epoxide of nitrophenyl benzoate

Preparation of 4-nitrophenyl 4'oxybenzoyl epoxypropyl ether

To a solution of 56 g (1 mole) of potassium hydroxide in 225 ml of water were added 69 g (0.5 mole) of p-hydroxybenzoic acid. To this solution were slowly added dropwise, at room temperature, 42 g (0.55 mole) of allyl chloride. Following the addition of the allyl chloride there was refluxing for a further 18 hours. After cooling the reaction mixture separated into two layers. A solution of 28 g (0.5 mole) of potassium hydroxide in 240 ml of water was added, and the whole was heated until a homogeneous reaction mixture had formed. After renewed cooling and acidification with concentrated hydrochloric acid 4(allyloxy)benzoic acid was precipitated. This product was recrystallised from 250 ml of glacial acetic acid. 32 g (0.18 mole) of the dried 4(allyloxy)benzoic acid were dissolved in 150 ml of thionyl chloride, whereupon 2 drops of dimethyl formamide were added and the whole was boiled with refluxing. Thionyl chloride was distilled off, and after being cooled the residue was incorporated into 100 ml of dry dichloromethane. After filtration the dichloromethane solution was added, with vigorous stirring, over 1 hour and at a temperature of 5°–10° C., to a solution of 23 g of nitrophenol (0.166 mole) in a mixture of 135 ml of dichloromethane and 34.2 ml of pyridine. There was 2 hours of afterstirring at room temperature. 250 ml of dichloromethane were added to the reaction mixture; the whole was washed twice with dilute hydrochloric acid and then washed until neutral. After distilling off of the solvents the residue was converted to the crystallised form from methanol. The yield was 37.6 g (70%).

10 g (33 mmoles) of 4-nitrophenyl 4'oxybenzoyl allyl ether were dissolved in 50 ml of dichloromethane, and 11.2 g (45.5 mmoles) of m-chloroperbenzoic acid were added under nitrogen. After 24 hours' stirring at room temperature 250 ml of dichloromethane were added, and the solution was washed with sodium carbonate solution and then with water until neutral. After drying and distilling off of the solvent the residue was converted to the crystallised form from 250 ml of ethanol. The yield was 8.1 g (77%).

The epoxide of nitrophenyl benzoate was used to prepare a liquid-crystalline polyether (LC 4) by using the general method for the synthesis of LC polyethers specified above, using nitrophenyl-(2,3- dihydroxypropyloxy)benzoate with an epoxy/OH ratio of 5:1. The diol was prepared in the same manner as the hexyloxy analogon in EP-A2-0 550 105. The molecular weight turned out to be 3173. Tg: 58°/63° C., Tc: 130° C.

Epoxide of methoxycyclohexyl benzoate

4(2,3 epoxypropyl oxy)phenyl 4'methoxycyclohexyl carboxylate 76 g (480 mmoles) of 4 methoxycyclohexane carboxylic acid (cis/trans mixture) were boiled for 7 hours with refluxing in 350 ml of thionyl chloride to which several drops of dimethyl formamide had been added. The obtained 4 methoxycyclohexane carboxylic acid chloride was composed almost completely of the trans compound. After distilling off of the thionyl chloride the residue was incorporated into 75 ml of dry tetrahydrofuran. At a temperature of from 0° to 5° C. this solution was slowly added dropwise to a solution of 158.4 g (1440 mmoles) of hydroquinone in 650 ml of tetrahydrofuran and 375 ml of pyridine. When, after this addition, the mixture had attained room temperature, it was poured onto ice and concentrated sulphuric acid. Extraction with dichloromethane, evaporation of the dichloromethane, and, in succession, conversion of the evaporation residue to the crystallised form from an ethanol-water mixture and from toluene gave a yield of 24.45 g (20%) of pure trans 4 hydroxyphenyl 4'methoxycyclohexyl carboxylate. 24.3 g (97 mmoles) of the above compound were boiled, with refluxing, for 24 hours with 17.6 g of allyl bromide (145 mmoles) and 13.4 g (97 mmoles) of potassium carbonate in 350 ml of methylethyl ketone. After cooling the reaction mixture was poured into 1 of ice water, which was extracted with the aid of diethyl ether. After drying and evaporation of the diethyl ether 28.9 g (97%) of 4 allyloxyphenyl 4'methoxycyclohexyl carboxylate were obtained. To 28.7 g (99 mmoles) of said compound in 250 ml of dichloromethane there were added 32.9 g of chloroperbenzoic acid, and the mixture was stirred for 24 hours under an atmosphere of nitrogen. After being diluted with dichloromethane the reaction mixture was washed with sodium carbonate solution and water. After drying the dichloromethane was distilled off, and the residue was purified on a column filled with silica gel and eluted with a hexane-ethyl acetate mixture (75/25). The yield was 20.8 g (66%) of 4(2,3 epoxypropyl oxy)phenyl 4'methoxycyclohexyl carboxylate.

The epoxide of methoxycyclohexyl benzoate was used together with the epoxide of methoxyphenyl benzoate to prepare a liquid crystalline polyether (LC 5) by using the general method for the synthesis of liquid crystalline polyethers specified above, using methoxy phenyl-(2,3 dihydroxypropyloxy) benzoate with an epoxy/OH ratio of 5:1. It appeared that the cyclohexyl group containing epoxide was present for 16 mole % in the polyether.

Example 3

Procedure for making the retardation layers:

Used were two glass substrates of a thickness of 100 micrometers. These were coated with Merck "LIQ-UICOAT®" PA (E. Merck, Fed. Rep. Germany), pre-cured at 60° C. for 15 minutes, cured at 300° C. for 1 hour, and then rubbed in the appropriate direction on a felt cloth, in accordance with the instructions provided by Merck. To ensure proper adhesion of the PI layer the glass substrates were cleaned in advance using the following procedure:

ultra-sonic cleaning with a detergent (Q9, Purum GmbH)

KOH (1 M), 50°C./1 hr $HNO_3/H_2SO_4/H_2O$ (1:1:10), 60°C/1 hr reflux in isopropyl alcohol vapour for 30 minutes or more.

Between each cleansing step a rinsing with demineralised water was performed. This is a variation on the method as described by W. H. de Jeu in *Physical properties of Liquid Crystals*, 1st edition (Gordon and Breach Science Publishers), p. 23.

LC 3 was dissolved in cyclopentanone together with 5 wt. % of chiral dopant (Merck CB 15™). To the filtered solution 0.5 wt. % (calculated on LC material 3) of cross-linked polymer spheres (Dynospeheres DL 1060®, ex JSR) was added as spacers. The solution of LC material 3 with spacers was spin-coated onto the two pretreated glass substrates. The layer thickness obtained was 4 micrometers. The two films of LC material 3 were dried in a vacuum oven for 16 hours at 20° C. They were then placed one on top of the other under a 60° difference in orientation direction and moulded at a temperature of 160° C. Next, the sample was cooled to 115° C., and after 5 minutes to room temperature. The quality of the resulting retardation film was determined with the aid of various optical techniques based on the theory described in E. P. Raynes, "The Optical Properties of Supertwisted Liquid Crystal Layers", *Molecular Crystals & Liquid Crystals Letters*, 4(3–4) (1987), 69–75.

Figure 2:
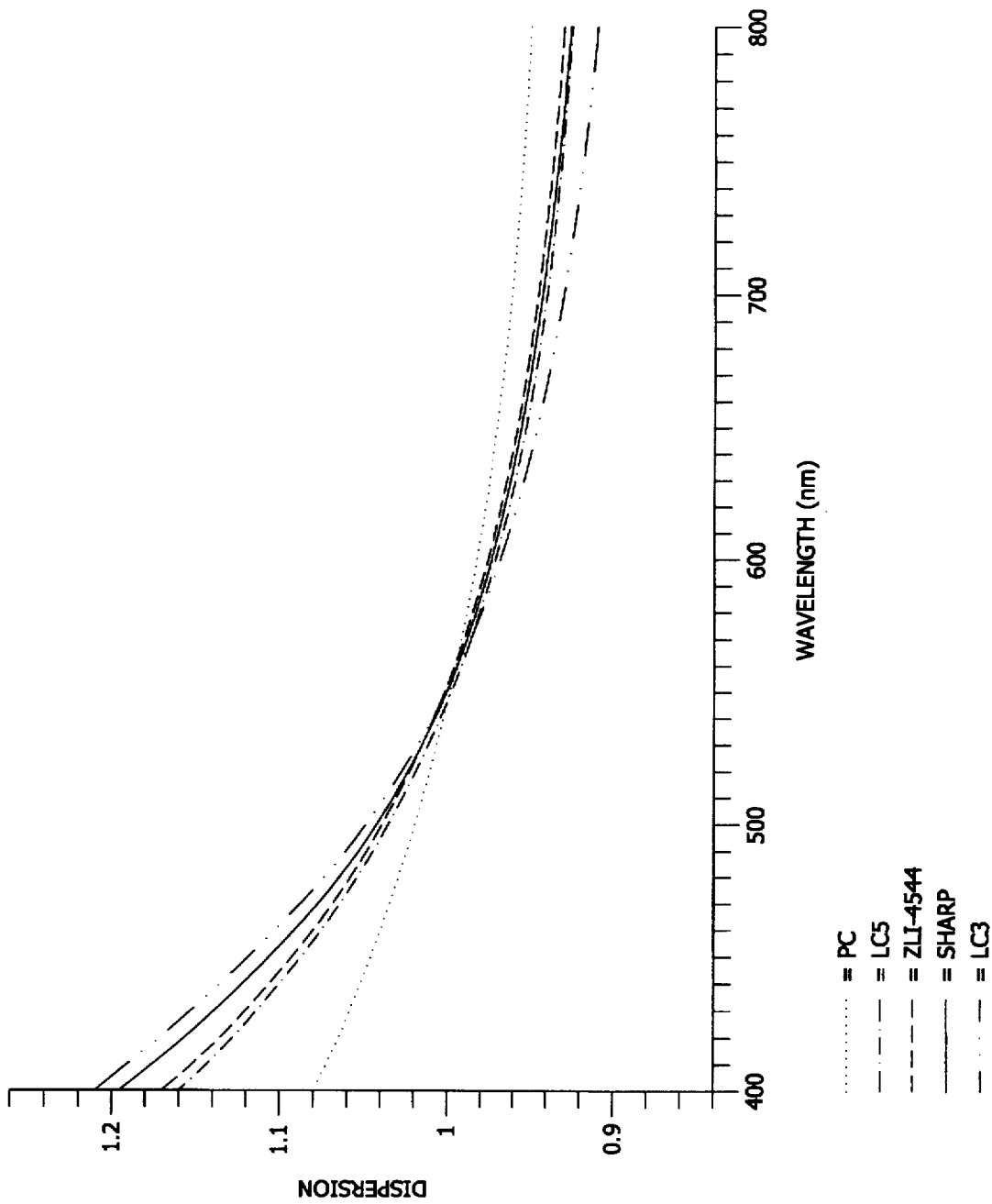
FIG. 2 shows the dispersion (defined as the retardation at a certain wavelength divided by the retardation at 550 nm) for LC 3, LC 5, an active cell used in the Sharp wordprocessor WD A 330 ("Sharp"), a polycarbonate film ("PC") and an active cell containing a commercially available liquid crystal mixture ZLI 4544 from Merck ("ZLI 4544").

The dispersion of the high-molecular weight liquid-crystalline material was measured by fitting transmission spectra of the retardation layers between two polarisers to the formulae given in Raynes. In FIG. 2 the dispersion (defined as the retardation at a certain wavelength divided by the retardation at 550 nm) was given for LC 3, a birefingent polycarbonate film such as described in *Jap. J. Appl Physics*, V01.30, No. 4 (April 1991), 682–686, and a commercially available low-molecular weight liquid-crystalline active cell as used in the Sharp wordprocessor WD A 330™, and an active cell containing a commercially available liquid crystal mixture ZLI 4544, ex Merck.

From FIG. 2 it can be seen that the dispersion of LC 3 according to the invention is nearly the same as that of a commercially available active cell (a difference in dispersion of less than 0.1) over the whole wavelength area of 400–800 nm, whereas the dispersion of the 30 birefringent polycarbonate film only matches that of the commercially available active cell at 550 nm , by definition, and shows large deviations, especially in the shorter wavelength area of 400–550 nm.

The dispersion of LC 5 is nearly the same as that of the active cell containing ZLI 4544 over the whole wavelength area of 400–800 nm.

Figure 3:
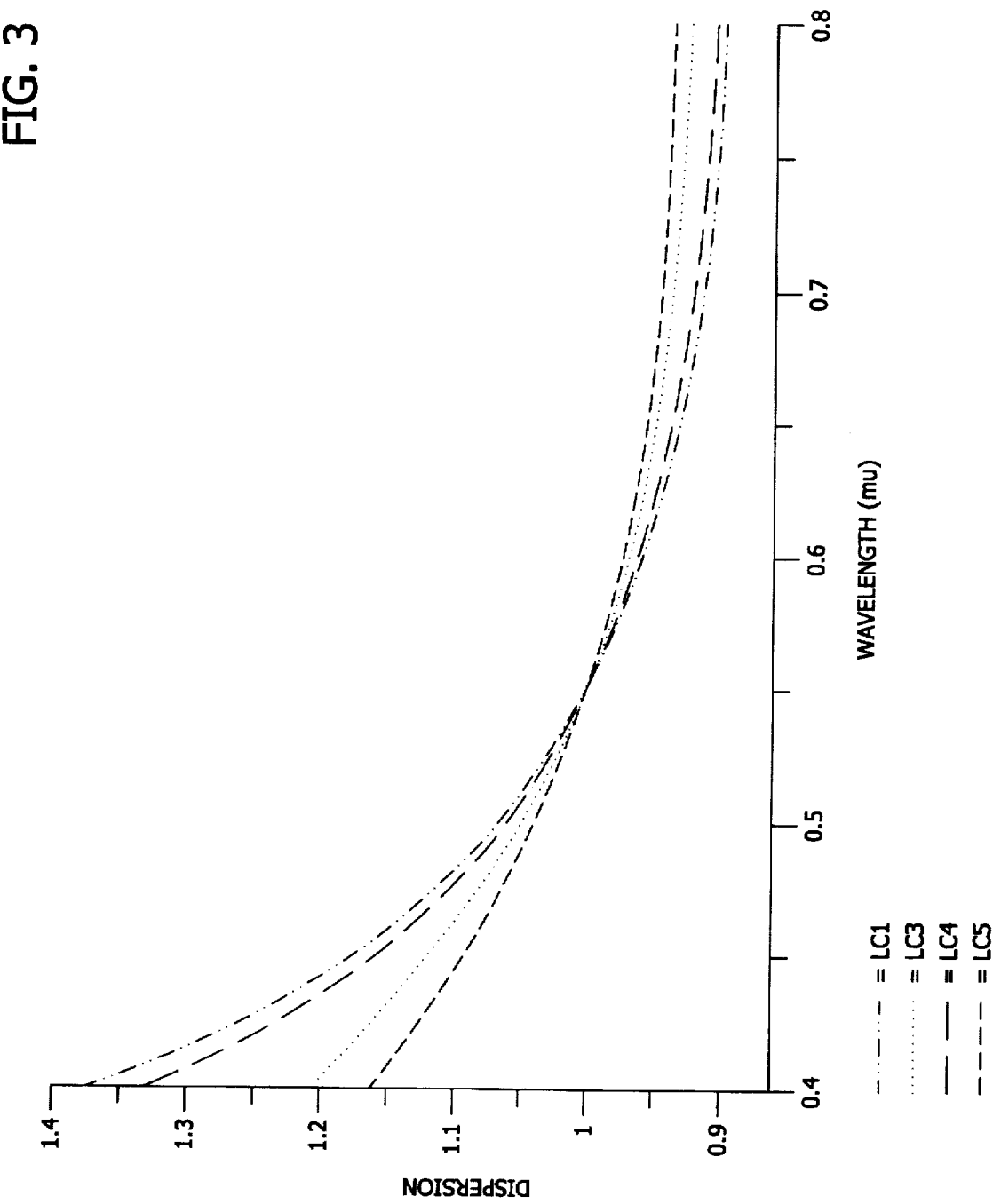
FIG. 3 shows the dispersion for various LC materials according to the invention.

In FIG. 3 the dispersion is given for various LC materials according to the invention. From FIG. 3 it can be seen that using mesogenic groups with a by more conjugated system such as cyanobiphenyl gives a higher dispersion than when LC material having mesogenic groups with a less conjugated system such as phenyl benzoate groups are used. A comparison between LC material having nitrophenyl benzoate mesogenic groups and LC material having methoxyphenyl benzoate mesogenic groups showed that the latter, i.e., the least conjugated material, has the lowest dispersion. When replacing some of the phenyl groups for cyclohexyl groups in the mesogenic groups, the dispersion is lowered even further. These examples show that the dispersion can be set by varying the mesogenic groups of the LC material.

We claim:

1. A method for making a liquid-crystalline display, which display comprises an active liquid-crystalline cell and a retardation layer comprising a high-molecular weight liquid-crystalline material comprising at least one mesogenic group, the method comprising adapting the dispersion of the retardation layer to that of the active liquid-crystalline cell by varying the mesogenic group or groups of the high-molecular weight liquid-crystalline material, so that the difference in dispersion between the active cell and the retardation layer in the wavelength area of 400–800 nm is not more than 0.1.

2. The method of claim 1, wherein the high-molecular weight liquid-crystalline material is placed between two orienting substrates, giving one of the substrates a different orientation direction from that of the other substrate.

3. A liquid crystalline display made by the method of claim 1.

4. The liquid-crystalline display of claim 3 wherein the high-molecular weight liquid crystallime material comprises at least one mesogenic group having a large conjugated system and at least one mesogenic group having a smaller conjugated system.

5. The method of claim 1 wherein the difference in dispersion between the active cell and the retardation layer in the wavelength area of 400–800 nm is not more than 0.03.

6. The method of claim 4 wherein the ratio of mesogenic groups with large and small conjugated systems is varied.

7. The method of claim 1 wherein the dispersion is adapted by varying polarity of the mesogenic group.

8. The method of claim 1 wherein the mesogenic group is halogenated.

* * * * *